United States Patent
Axelsson et al.

(10) Patent No.: US 8,987,475 B2
(45) Date of Patent: Mar. 24, 2015

(54) PROCESS FOR PREPARING CYCLOLIGNANS

(75) Inventors: Magnus Axelsson, Järfälla (SE); Ulf Bremberg, Uppsala (SE); Auri Linden, Stockholm (SE); Fredrik Von Kieseritzky, Stockholm (SE)

(73) Assignee: Alexar AB, Solna (SE)

( * ) Notice: Subject to any disclaimer, the term of this patent is extended or adjusted under 35 U.S.C. 154(b) by 24 days.

(21) Appl. No.: 13/819,514

(22) PCT Filed: Aug. 30, 2011

(86) PCT No.: PCT/SE2011/051034
§ 371 (c)(1),
(2), (4) Date: Mar. 15, 2013

(87) PCT Pub. No.: WO2012/030284
PCT Pub. Date: Mar. 8, 2012

(65) Prior Publication Data
US 2013/0245285 A1    Sep. 19, 2013

Related U.S. Application Data

(60) Provisional application No. 61/378,435, filed on Aug. 31, 2010.

(30) Foreign Application Priority Data

Aug. 31, 2010    (SE) ...................................... 1050894

(51) Int. Cl.
  C07D 307/77    (2006.01)
  C07D 493/04    (2006.01)

(52) U.S. Cl.
  CPC .................................. C07D 493/04 (2013.01)
  USPC ....................................................... 549/298

(58) Field of Classification Search
  CPC .................................................... C07D 493/04
  USPC ....................................................... 549/298
  See application file for complete search history.

(56) References Cited

U.S. PATENT DOCUMENTS

| 5,013,851 | A | 5/1991 | Kaneko et al. |
| 2013/0317099 | A1 | 11/2013 | Bisrat et al. |
| 2013/0331445 | A1 | 12/2013 | Bisrat et al. |

FOREIGN PATENT DOCUMENTS

| CN | 101389326 | 3/2009 |
| CN | 101492704 | 7/2009 |
| EP | 0522173 | 1/1993 |
| JP | 2005500300 | 1/2005 |
| JP | 6009642 | 2/2011 |
| WO | WO-02-102804 | 12/2002 |
| WO | WO-2007-097707 | 8/2007 |
| WO | WO-2009100349 | 8/2009 |
| WO | WO-2009-157858 | 12/2009 |

OTHER PUBLICATIONS

International Search Report for PCT/SE2011/051034, mailed Nov. 30, 2011.
Written Opinion for PCT/SE2011/051034, mailed Nov. 30, 2011.
Stadler, et al., Concise stereoselective synthesis of (−)-Podophyllotoxin by an intermolecular iron(III)-catalyzed Friedel-Crafts alkylation, Angewandte Chemie, 2008, vol. 47(39), pp. 7557-7559.
Wu, et al., Enantioselective sequential conjugate addition-allylation reactions: A concise total synthesis of (+)-Podophyllotoxin, Organic Letters, 2009, vol. 11(3), pp. 597-600.
Sengupta, et al., Intramolecular Heck reaction strategy for the synthesis of functionalized tetrahydroanthracenes: a facile formal total synthesis of the linear abietane diterpene, umbrosone, Tetrahedron Letters, 2005, vol. 46(9), pp. 1515-1519.
International-Type Search Report for Search Request No. ITS/SE10/00264, mailed Feb. 22, 2011.
Buchardt, et al., "Thermal Chemistry of Podophyllotoxin in Ethanol and a Comparison of the Cytostatic Activity of the Thermolysis Products," Journal of Pharmaceutical Sciences, Nov. 1986, pp. 1076-1080, vol. 75, No. 11.
Casey, et al., "A concise stereocontrolled formal total synthesis of (±)-podophyllotoxin using sulfoxide chemistry," Chem. Commun., 2004, pp. 184-185.
Inamoto, et al, "Highly Efficient Nickel-Catalyzed Heck Reaction Using Ni(acac)$_2$/N-Heterocyclic Carbene Catalyst," Synlett, 2005, pp. 1624-1626, vol. 10.
Lear, et al., "Synthesis and biological evaluation of carbon-substituted C-4 derivatives of podophyllotoxin," Can. J. Chem., 1995, pp. 1704-1708, vol. 74.
Li, et al., "Synthesis of functionalized acetophenone," Journal of Chemical Research, 2006, pp. 388-389.
Sengupta, et al., "Intramolecular Heck reaction strategy for the synthesis of functionalized tetrahydroanthracenes: a facile formal total synthesis of the linear abietane diterpene, umbrosone," Tetrahedron Letters, 2005, pp. 1515-1519, vol. 46.

(Continued)

*Primary Examiner* — Nizal Chandrakumar
(74) *Attorney, Agent, or Firm* — White & Case LLP

(57) ABSTRACT

The invention relates to a one-pot reaction for the preparation of a compound of Formula (I). The compound of Formula (I) may be further transformed into picropodophyllin and derivatives thereof.

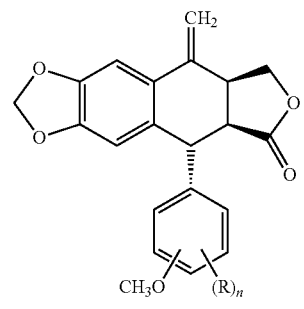

26 Claims, No Drawings

(56) References Cited

OTHER PUBLICATIONS

Stadler, et al., "Concise Stereoselective Synthesis of (−)-Podophyllotoxin by an Intermolecular Iron (III)-Catalyzed Friedel-Crafts Alkylation," Angew. Chem. Int. Ed., 2008, pp. 7557-7559, vol. 47.

Tietze, et al., "Towards a Total Synthesis of the New Anticancer Agent Mensacarcin: Synthesis of the Carbocyclic Core," Chem. Eur. J., 2004, pp. 5233-5242, vol. 10.

Tietze, et al., "Intramolecular Heck Reactions for the Synthesis of the Novel Antibiotic Mensacarcin: Investigation of Catalytic, Electronic and Conjugative Effects in the Preparation of the Hexahydroanthracene Core," Eur. J. Org. Chem., 2005, pp. 1752-1759, vol. 9.

Wu, et al., "Enantioselective Sequential Conjugate Addition—Allylation Reactions: A Concise Total Synthesis of (+)-Podophyllotoxin," Organic Letters, 2009, pp. 597-600, vol. 11, No. 3.

Ackermann, et al., "Mizoroki-Heck Reactions with Metals Other than Palladium" in *The Mizoroki-Heck Reaction*, 2009, pp. 383-403, John Wiley & Sons, Ltd., Chichester, United Kingdom.

"Arylation and Alkylation of Alkenes by Organopalladium Compounds: The Heck Reaction" in *Advanced Organic Chemistry*, 5$^{th}$ Ed., 2001, pp. 930-931, Section 14-19, John Wiley & Sons, Inc., New York.

Abad-Reyes, et al., "Productos inesperados en la transformación química de derivados de la podofilotoxona a través de la reacción de Takai," Avances en Química, 2008, pp. 27-34, vol. 3, No. 1.

Gensler, et al., "The Podophyllotoxin-Picropodophyllin Equilibrium," J. Org. Chem., Oct. 1966, pp. 3224-3227, vol. 31.

Beletskaya et al., "Palladacycles in catalysis—a critical survey," J. Organomet. Chem., 2004, pp. 4055-4082, vol. 689.

Lipshutz et al., "Heck Couplings at Room Temperature in Nanometer Aqueous Micelles," Org. Lett., 2008, pp. 1329-1332, vol. 10, No. 7.

Dounay et al. Chem. Rev. 2003, 103, 2945-2963.

Gibson et al. Contemp. Org. Synth., 1996, 3, 447-471.

PROCESS FOR PREPARING CYCLOLIGNANS

This application is the U.S. national stage of PCT/SE2011/051034, filed on Aug. 30, 2011, which claims priority to U.S. provisional patent application Ser. No. 61/378,435, filed on Aug. 31, 2010 and to Swedish patent application no. SE 1050894-3, filed on Aug. 31, 2010.

FIELD OF THE INVENTION

The present invention relates to a process for the preparation of cyclic compounds which may be further transformed into picropodophyllin and derivatives thereof. More specifically, the invention relates to a one-pot reaction for the preparation of polycyclic lignans involving ring closure and epimerization.

BACKGROUND OF THE INVENTION

Picropodophyllin is a compound belonging to the class of compounds denominated cyclolignans. The chemical structure of picropodophyllin is complex with a fused cyclic ring system and four adjacent chiral centra. The stereochemistry of the lactone ring exhibits a cis configuration by having two beta carbon-carbon bonds, i.e. the 8-9 and 8'-9' bonds are located in or above the plane of the carbon ring. The hydroxy group and the trimethoxy benzyl ring are connected to the 7 and 7' carbons, respectively, by alpha-bonds.

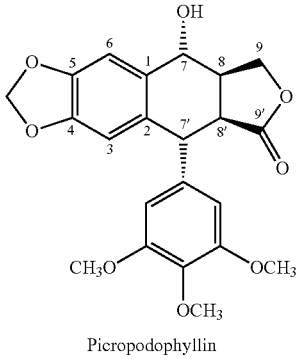

Picropodophyllin

For a long time, picropodophyllin attracted little interest, since it was believed to possess no or low biological activity. In contrast, its stereoisomer podophyllotoxin, which has a trans configuration in the lactone ring, has been studied for decades due to its cytotoxic properties. Podophyllotoxin is also the starting material for the synthesis of Etoposide and other topoisomerase II inhibitors.

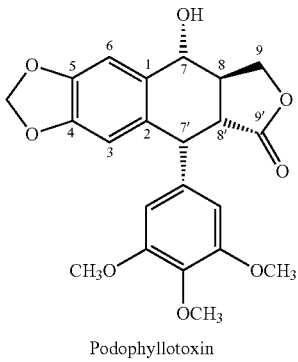

Podophyllotoxin

However, research has revealed that picropodophyllin does indeed exhibit interesting biological properties.

In WO 02/102804 it is disclosed that picropodophyllin is a specific and potent inhibitor of insulin-like growth factor-1 receptor (IGF-1R) and may be used in the treatment of IGF-1R dependent diseases such as various types of cancer, for instance malignant melanoma, Ewing's sarcoma, breast cancer, prostate cancer and leukemia, as well as in the treatment of psoriasis, arteriosclerosis and acromegaly. It is also mentioned that picropodophyllin may be used to potentiate the effects of anti-cancer drugs.

WO 2007/097707 discloses the use of picropodophyllin in the prophylaxis or treatment of diabetes mellitus type 2, nephropathy, retinopathy, macular degeneration, retinopathy of prematurity, central retinal vein occlusion, branch retinal vein occlusion, rubeotic glaucoma, thyroid eye disease, corneal graft rejection and corneal chemical burns; and for contraception.

WO 2009/157858 discloses the use of picropodophyllin for prophylaxis or treatment of diseases or conditions characterized by a hyperactive immune system such as rheumatoid arthritis, Crohn's disease, ulcerative colitis, multiple sclerosis, Alzheimer's disease, asthma, eczematous dermatitis, and graft rejection following transplantation.

Usually, picropodophyllin is obtained from its stereoisomer podophyllotoxin by epimerization. The major source of podophyllotoxin is several podophyllum species which mainly can be found in China. Because of the ease of extraction, *Podophyllum emodi* is a highly preferred plant, but this plant is difficult to cultivate and is becoming extinct in the wild which has caused the Chinese government to give this plant the highest level of protection. *Podophyllum peltatum* and *Podophyllum versipelle* constitute other plant sources of podophyllotoxin, but yield less pure podophyllotoxin upon extraction. Extraction of the podophyllum species yields podophyllotoxin, which has to be handled with great care because of its cytotoxic properties. The lack of easy access to the podophyllum species, the need for cautious handling of the poisonous plants and the cytotoxic podophyllotoxin, and the fact that podophyllum species are also used for extraction of other biologically active compounds are all factors that contribute to a high cost of goods and uncertain availability of podophyllotoxin as well as picropodophyllin.

A method converting podophyllotoxin into picropodophyllin is disclosed in *Journal of Pharmaceutical Sciences*, Vol. 75, No. 11, November 1986, Ole Buchardt et al., pages pp. 1076-1080. The yield of pure picropodophyllin is reported to be 78%.

The complex structures of podophyllotoxin and picropodophyllin have made them attractive targets for organic chemists interested in total synthesis of structurally complex compounds exhibiting biological activity, sometimes also with the aim of finding a synthetic route suitable to being performed on a large scale. Most of the published total synthesis aim at synthesizing podophyllotoxin, the drawbacks of which have been indicated above, which is subsequently epimerized into picropodophyllin at the end of the reaction sequence. For instance, synthetic routes involving epimerization of podophyllotoxin into picropodophyllin are described in *Angew. Chem., Int. Ed.*, 2008, 47, p. 7557 and *Org. Lett.*, 2009, 11(3), p. 597. It is a disadvantage to perform a crucial chemical reaction step at the end of a long reaction sequence since the value of the material, i.e. the compound undergoing transformations in the reaction sequence, increases with each reaction step and a failure at a late stage of the synthesis will therefore be expensive. Some publications mention synthetic routes wherein picropodophyllin is formed without going via podophyllotoxin. For instance, *Angew. Chem., Int. Ed.,* 2008, 47, p. 7557 mentions such a route, but this route also produces a substantial amount of a by-product.

The synthetic route to podophyllotoxin (which can then be isomerized to picropodophyllin) used in *Angew. Chem., Int. Ed.,* 2008, 47, p. 7557 is depicted in Scheme I.

Scheme I

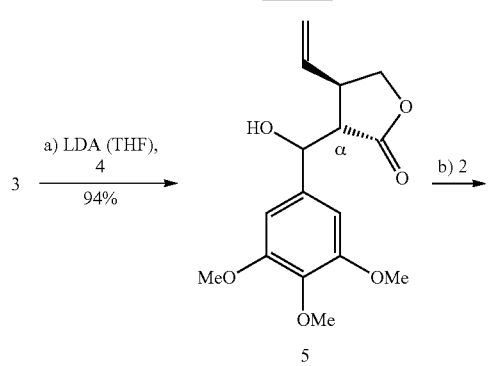

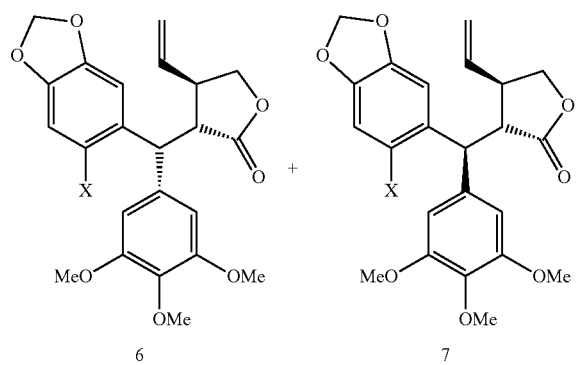

2 = Sesamol; 3 = Taniguchi lactone; 4 = Trimethoxybenzaldehyde; X = OH;
Conditions: a) Lithium diisopropylamide (1.1 equiv). THF, -78° C., 30 min. then 4 (1.1 equiv). -78° C., 3 h, 94% (d.r. 52:48); b) DCM, FeCl₃, rt. 60 min. 99%

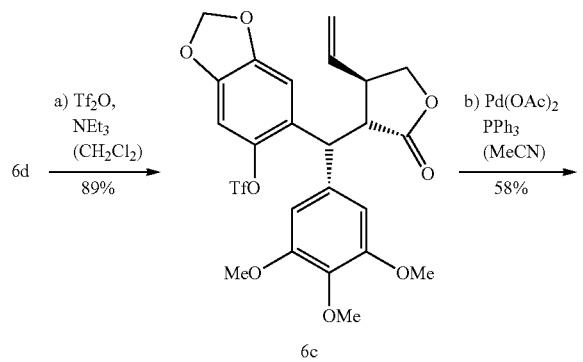

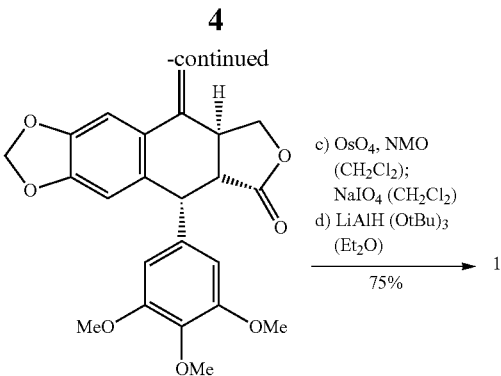

1 = Podophyllotoxin; 6d = 6 with X = OH. Conditions: a) Tf₂O (1.5 equiv). NEta(2 equiv). CH₂Cl₂, 0° C., 1 h, 89%; b) Pd•(OAc)₂ (10 mol %). PPh₃ (0.3 equiv). K₂CO₃ (3 equiv), MeCn, 80° C., 20 h. 58%; c) OsO₄ (5 mol %). NMO (3 equiv), CH₂Cl₂, 20° C., 4 h, then NaIO₄ (2 equiv). 30 min. 95%; d) LiAlH (OtBu)₃ (10 equiv). Et₂O. -78 + 20° C., 18 h, 79% (d.r. 98:2).

Another publication mentioning a synthetic route for formation of picropodophyllin without going via podophyllotoxin is described in *Chem. Commun.*, 2004, p. 184. However, when the inventors attempted to repeat this synthetic route problems were encountered during the synthesis of the enantiopure sulfoxide starting material. The difficulties of making the sulfoxide were confirmed by the authors of the Chem. Comm. article.

Thus, there remains a need for improved synthesis of picropodophyllin and derivatives thereof.

Abbreviations
Cat. Catalytic
dba Dibenzylideneacetone
DCM Dichloromethane
DMSO Dimethyl Sulfoxide
equiv. Equivalents
EtOAc Ethyl acetate
g Gram
h Hour
HPLC High Performance Liquid Chromatography
LCMS Liquid Chromatography Mass spectrometry
M Molar
MS Mass Spectrosopy
mg Milligram
min Minute
mL Milliliter
mm Millimeter
mmol Millimol
NMO N-Methylmorpholine-N-Oxide
NMR Nuclear Magnetic Resonance
Pd(dppf)DCM: Pd(dppf)Cl₂.CH₂Cl₂[1,1'-Bis(diphenylphosphino) ferrocene]dichloropalladium(II), complex with dichloromethane
Pd₂(dba)₃ Tris(dibenzylideneacetone)dipalladium(0)
r.t. Room Temperature
Rt Retention time
Tf Triflyl, more formally known as trifluoromethanesulfonyl
OTf Triflate, more formally known as trifluoromethanesulfonate
TFA Trifluoro Acetic Acid
s singlet
d doublet
dd doublet of doublet
m multiplet
app apparent
wt-% Weight-%
vol-% Volume-%
Å Angstrom

DESCRIPTION OF THE INVENTION

It is an object of the present invention to overcome or at least mitigate some of the disadvantages associated with the prior art.

The present invention is based on the unexpected finding that it is possible to epimerize and cyclize a compound of Formula (V) in a one-pot reaction using Heck reaction conditions.

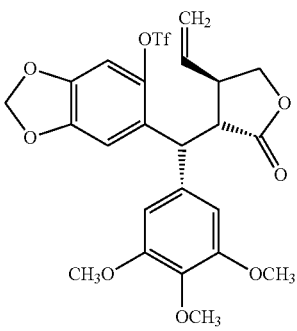

V

The resulting product is a compound of Formula (III) having a cis configuration in the lactone ring by having two beta carbon-carbon bonds, i.e. the 8-9 and 8'-9' bonds are located above the plane of the carbon ring.

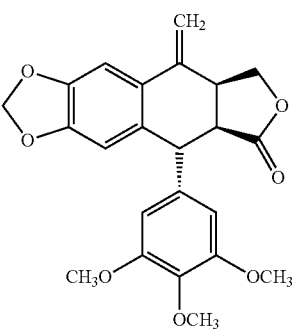

III

The compound of Formula (III) may be used in the synthesis of, for instance, picropodophyllin and analogues thereof.

In this document, the expression Heck reaction conditions is understood to mean a stoichiometric or catalytic amount of one or more transition metal compounds, such as palladium or nickel compounds, which may be the same or different, in the presence of a base. The transition metal compounds, such as palladium or nickel compounds, may be added to the reaction mixture or generated in situ in the reaction mixture. Typically, the transition metal is palladium. Further, the palladium compound may be Pd(0), i.e. palladium in the oxidation state zero, Pd(0) attached to one or more ligands or palladium in other oxidation states capable of generating an active Heck catalyst. The Heck reaction is described in the textbook Advanced Organic Chemistry, 5$^{th}$ to; Smith, M. B., March, J.; Section 14-19, pages 931-932. Nickel transition metal compounds may be Ni(0) or Ni(II). For examples of Heck reactions using nickel catalysts, see for instance Li; Pei, W.; Chen, S. J. Chem. Res. 2006, pp. 388-389. and Inamoto, K.; Kuroda, J.; Danjo, T.; Sakamoto, T. Synlett 2005, pp. 1624-1626. and for a review, see: Ackermann, L.; Born, R. Mizoroki-Heck Reactions with Metals Other than Palladium. In The Mizoroki-Heck Reaction; Oestreichq, M., Ed.; John Wiley & Sons Ltd.: Chichester, U. K., 2009; pp 383-403. (DOI:10.1002/9780470716076.ch10)

The one-pot reaction presents the advantages of determining the stereochemistry of the lactone ring into the desired cis configuration at an early stage of the reaction sequence, thereby shortening the synthetic route to picropodophyllin as well as avoiding handling of the cytotoxic podophyllotoxin.

One aspect the present invention provides a one-pot process for the preparation of a compound of Formula (I)

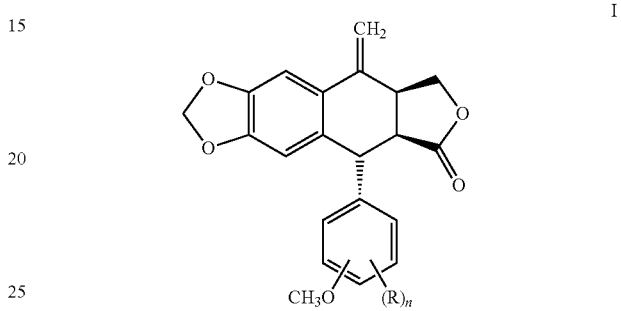

I wherein

R, which may be the same or different, is OH, OCH$_3$, OCH$_2$CH$_3$, F, Cl, CH$_3$ or CF$_3$, and n is 0, 1, 2, 3, or 4; comprising cyclization of a compound of Formula (II)

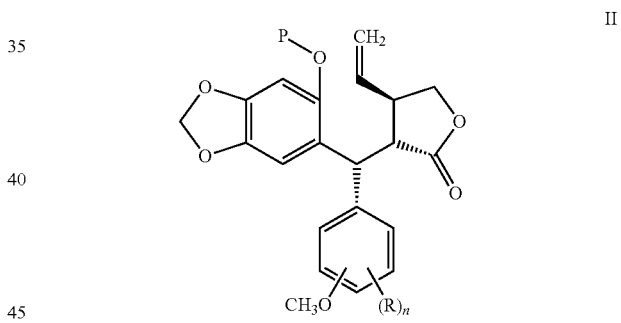

II wherein

R and n are as defined for Formula (I); and

P is an activating group;

in the presence of
  i. a base;
  ii. a protic solvent, or a mixture of a protic and an aprotic solvent;
  iii. and a transition metal component;
said process being performed under Heck reaction conditions.

In one aspect of the invention the transition metal component is selected from Pd(0), a compound containing Pd(II), a compound containing Pd(0), a mixture of compounds containing Pd(II) and Pd(0), and a mixture of Pd(0) and a compound containing Pd(II) and/or Pd(0).

In a further aspect of the invention, the transition metal component is Ni(0) or Ni(II), such as Nickel acetate tetrahydrate —Ni(II)(OAc)$_2$.4H$_2$O having the CAS number 6018-89-9 or Nickel(II) acetylacetonate —Ni(II)(acac)$_2$ having the CAS #3264-82-2

In yet an aspect of the invention, the transition metal component is the Hermann-Beller catalyst, having the chemical name trans-Di(μ-acetato)bis[o-(di-o-tolyl-phosphino)benzyl]dipalladium(II) and the CAS #172418-32-5.

In still an aspect of the invention, the transition metal component is Pd-118 (PdCl$_2$(dtbpf)), having the chemical name 1,1'-Bis(di-tert-butylphosphino)ferrocene]dichloropalladium(II) and the CAS #95408-45-0.

In one aspect of the invention, the transition metal complex is Pd(dppf)Cl$_2$.CH$_2$Cl$_2$ (Pd(dppf).DCM), having the chemical name [1,1'-Bis(diphenylphosphino)ferrocene]-dichloropalladium(II).

While not wishing to be bound by any specific theory, it is believed that the activating group P acts by activating the palladium catalyzed oxidative addition step of Heck cyclization, In one aspect of the invention there is provided a process wherein R in Formula (I) and (II) is OCH$_3$.

In yet an aspect of the invention there is provided a process as herein described, for the preparation of a compound of Formula (III)

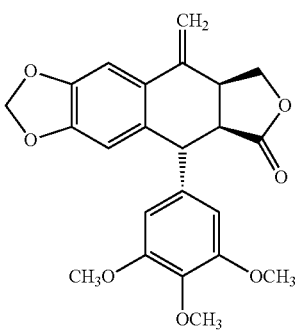

III comprising cyclization of a compound of Formula (IV)

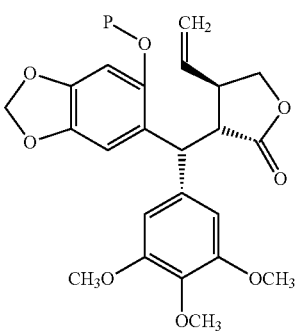

IV wherein P is an activating group.

In one aspect of the invention there is provided a process as herein described, wherein the activating group P is selected from the group consisting of trifluoromethanesulfonate, methanesulfonate, ethanesulfonate, benzenesulfonate, toluenesulfonate and 4-nitrobenzenesulfonate.

In still an aspect of the invention there is provided a process as herein described, wherein the base is an inorganic base, such as an inorganic base selected from the group consisting of K$_2$CO$_3$, Na$_2$CO$_3$, KHCO$_3$, NaHCO$_3$, NaOH, Cs$_2$CO$_3$, KOH, NaOH, Na$_3$PO$_4$, Na$_2$HPO$_4$, K$_3$PO$_4$, K$_2$HPO$_4$, and NH$_4$OH.

In yet an aspect of the invention the base may be an amine base such as ammonia, trimethyl amine, triethyl amine and diisopropyl ethylamine.

In yet an aspect of the invention there is provided a process as herein described, wherein the compound containing Pd(0) is selected from the group consisting of Pd(dppf).DCM, tetrakis(triphenylphosphine)Pd(0), Pd$_2$(dba)$_3$, dichlorobis(triphenylphosphine)palladium(0), palladium(II) acetate, palladium(II) acetate triphenylphosphine, palladium(II) chloride, palladium(II) chloride triphenylphosphine and palladium black.

In one aspect of the invention, there is provided a process as herein described, wherein the solvent is a protic solvent.

In one aspect of the invention there is provided a process as herein described, wherein the protic solvent is selected from the group consisting of methanol, ethanol, propanol, isopropanol, butanol and tert-butanol.

In one aspect of the invention there is provided a process as herein described, wherein the solvent comprises 0.001-50 vol-% of water.

In still an aspect of the invention there is provided a process as herein described, wherein the solvent comprises 2-20 vol-% of water.

In an aspect of the invention there is provided a process as herein described, wherein the solvent comprises 0.001-20 vol-% of water.

In yet an aspect of the invention, the solvent comprises 5 vol-% of water.

In one aspect of the invention there is provided a process as herein described, further comprising heating during the cyclization of the compound of Formula (II).

In one aspect of the invention there is provided a method of making picropodophyllin or derivatives thereof, comprising a process according to any previous aspect and as herein described.

In a further aspect of the invention, there is provided a method of making 4'-demethoxy-picropodophyllin comprising a process according to any previous aspect and as herein described.

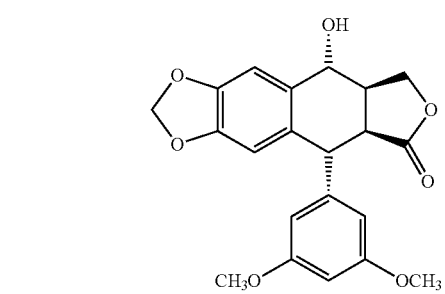

4'-Demethoxy-picropodophyllin

In an aspect of the invention, the heating during the cyclization of the compound of Formula (II) may take place at a temperature of from room temperature to 150° C.

In yet an aspect of the invention, the heating during the cyclization of the compound of Formula (II) may take place at a temperature of from 40° C. to 120° C.

In a further aspect of the invention, the heating during the cyclization of the compound of Formula (II) may take place at a temperature of from 30° C. to 100° C.

In one aspect of the invention, the heating during the cyclization of the compound of Formula (II) may take place at a temperature of from 40° C. to 90° C.

In one aspect of the invention, the heating during the cyclization of the compound of Formula (II) may take place at a temperature of from 60° C. to 80° C.

In one aspect of the invention, the heating during the cyclization of the compound of Formula (II) may take place at a temperature of from 50° C. to 80° C.

In still an aspect of the invention, the heating during the cyclization of the compound of Formula (II) may take place at a temperature of from 70° C. to 80° C.

In a further aspect of the invention, the cyclization of the compound of Formula (II) may take place in a mixture of solvents. It is to be understood that such solvents may be protic or aprotic. Examples of protic solvents that may be used in the cyclization are methanol, ethanol, propanol, iso-propanol, butanol and tert-butanol. Examples of aprotic solvents that may be used in the cyclization are acetonitrile, dimethylsulfoxide, tetrahydrofuran, dimethylformamide, N-methylpyrrolidone and dioxane.

In one aspect of the invention, the compound of Formula (V) is cyclized into the compound of Formula (III) as depicted in Scheme II below.

Scheme II

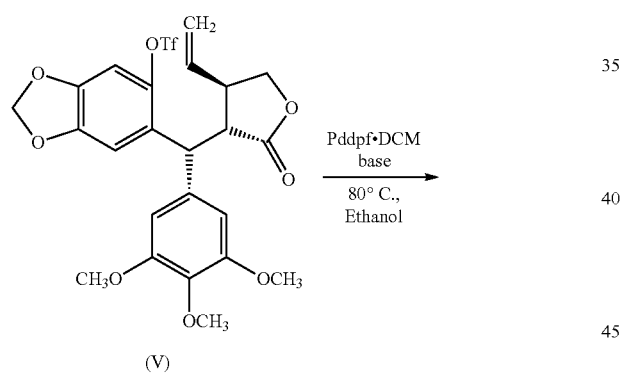

The cyclization reaction of the invention was successfully used in the synthesis of picropodophyllin as depicted in Scheme III below.

Scheme III

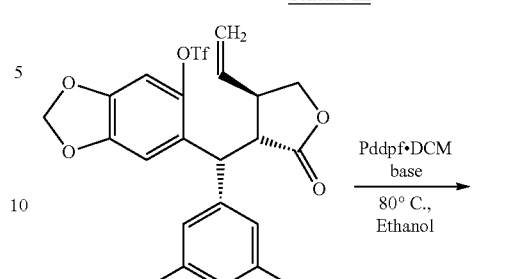

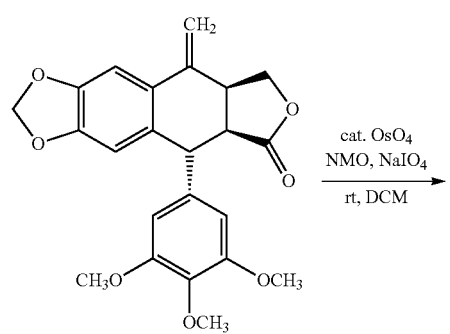

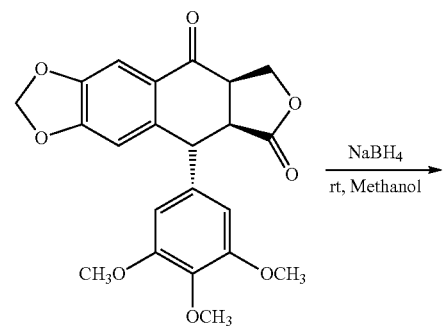

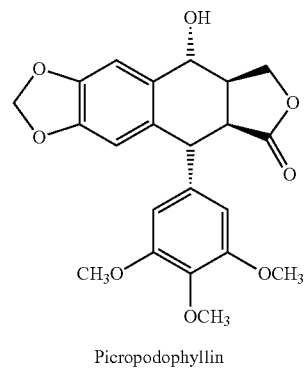

Picropodophyllin

In still an aspect of the invention, the compound of Formula (V) is cyclized into the compound of Formula (III) as depicted in Scheme IV below.

Scheme IV

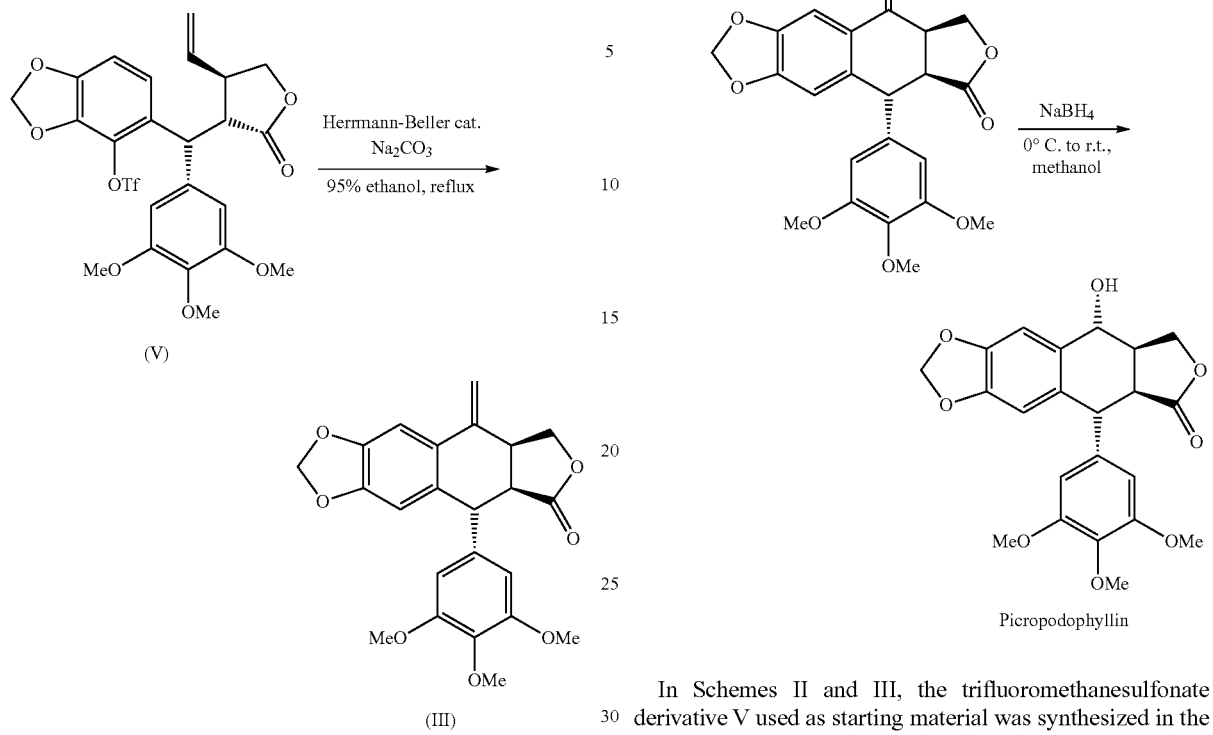

In yet an aspect of the invention, the cyclization reaction of the invention was successfully used in the synthesis of picropodophyllin as depicted in Scheme V below.

Scheme V

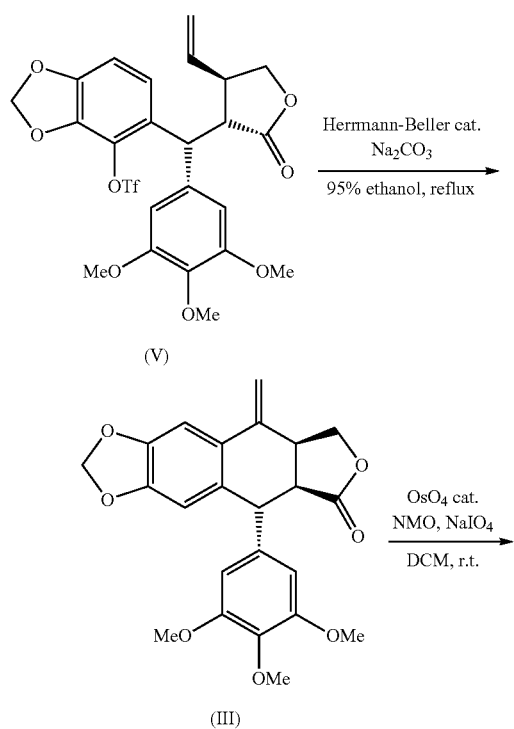

In Schemes II and III, the trifluoromethanesulfonate derivative V used as starting material was synthesized in the same way as compound 6c depicted in Scheme I. Comparison with Scheme I leading to podophyllotoxin (which then requires an isomerization step to picropodophyllin) shows that the process of the invention shortens the reaction sequence to picropodophyllin by one step, and also presents the advantage of having the epimerization to picropodophyllin at an early stage.

All commercial starting materials were purchased from Sigma-Aldrich, Fluke, TCl and Merck and were used as received without further purification.

The above aspects and embodiments may be combined with any other embodiment, aspect or claim of the invention described hereinbefore or hereinafter.

The invention is illustrated, but not limited, by the following Examples.

EXAMPLES

General Example Experimental Procedures

All solvents used were of HPLC grade or better, when anhydrous conditions were required an excess of 3 Å molecular sieves were added to a portion of the solvent at least 24 h before use to ensure dryness. $^1$H Nuclear magnetic resonance (NMR) was recorded on a Bruker Advance DPX 400 spectrometer at 400.1 MHz. Low-resolution electrospray ionization mass spectra were obtained using an Agilent mass spectrometer, in either positive or negative ionization mode. Flash chromatography was performed on Merck silica gel 60 (230-400 mesh). Analytical LCMS data were obtained with an Agilent mass spectrometer; Agilent 1100 system; ACE 3 C8 column, (50×3.0 mm, 5 μM); Gradient: 10-97% acetonitrile in water/0.1% TFA, in 3 min (flow: 1.0 mL/min); or Agilent mass spectrometer; Agilent 1100 system; Xterra C18 column (50×3.0 mm, 5 μM); Gradient: 10-97% acetonitrile in water/ 10 mM NH$_4$HCO$_3$ at pH10, in 3 min; (flow: 1.0 mL/min). Names of chemical structures were determined using Marvin Sketch 5.2.6, ChemAxon.

Example 1

Synthesis of (11S,15S)-16-methylidene-10-(3,4,5-trimethoxyphenyl)-4,6,13-trioxatetracyclo[7.7.0.0^{3,7}.0^{11,15}]hexadeca-1,3(7),8-trien-12-one

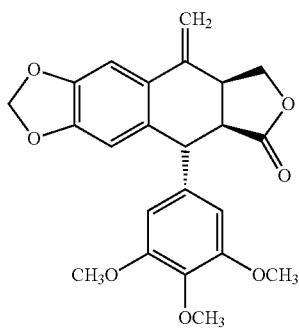

6-{[(4R)-4-ethenyl-2-oxooxolan-3-yl](3,4,5-trimethoxyphenyl)methyl}-2H-1,3-benzodioxol-5-yl trifluoromethanesulfonate (2.20 g, 3.93 mmol) (obtained according to Stadler, D.; Bach, T. Angew. Chem., Int. Ed., 2008, 47, 7557-7559.) was dissolved in 95% ethanol. Pd(dppf).DCM (0.96 g, 1.18 mmol) and K$_2$CO$_3$ (1.63 g, 11.8 mmol) were added and after short stirring the reaction was heated at 80° C. for 60 min. The reaction mixture was filtered through a pad of silica topped with celite and evaporated. The residue was dissolved in dichloromethane and filtered again through a pad of silica topped with celite. The crude product obtained by evaporation in vacuo (0.83 g, 51%) was isolated as a yellow-orange solid. Silica chromatography eluting with Pentane:EtOAc 1:1→1:2. LCMS: ACE 3 C8, 50×3.0 mm, 10%-97% methanol in 0.1% TFA in water, 1 mL/min; 80%, MS: 428 (100), 411, 429. $^1$H-NMR (400 MHz, CDCl$_3$): δ [ppm]=3.67-3.82 (m, 3H), 3.85 (s, 6H), 3.90 (s, 3H), 3.98 (app. s, 1H), 4.0 (d, 1H), 4.95 (d, 1H), 5.11 (d, 1H), 5.92 (app. s, 1H), 5.94 (app. s, 1H), 6.23 (s, 1H), 6.50-6.55 (m, 2H), 6.85 (s, 1H).

Example 2

Synthesis of (11R,15S)-16-(3,4,5-trimethoxyphenyl)-4,6,13-trioxatetracyclo[7.7.0.0^{3,7}.0^{11,15}]hexadeca-1,3(7),8-triene-10,14-dione

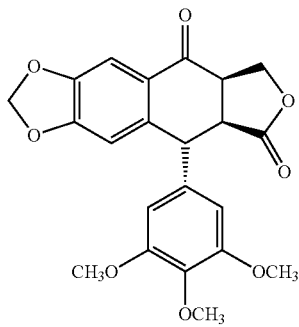

(11S,15S)-16-Methylidene-10-(3,4,5-trimethoxyphenyl)-4,6,13-trioxatetracyclo[7.7.0.0^{3,7}.0^{11,15}]hexadeca-1,3(7),8-trien-12-one obtained in Example 1 (0.730 g, 1.22 mmol) and N-methyl morpholine oxide (50 wt-% solution in water, 1.25. mL, 5.34 mmol) were suspended in dichloromethane (60 mL). Osmium tetroxide (4 wt-% solution in water, 0.37 mL, 0.060 mmol) was added to the suspension. The mixture was stirred vigorously at rt. After most of starting material had been consumed (over week-end), NaIO$_4$ (0.52 g, 2.44 mmol) was added and the reaction was stirred for an additional 30 min. The reaction was quenched by addition of aqueous sodium thiosulfate (50 mL) and the phases were separated. The aqueous phase was extracted with dichloromethane (2×50 mL) and the combined organic layers were washed with brine, dried over Na$_2$SO$_4$, filtered and evaporated to give 630 mg (85% yield) of the product in 75% purity. Another batch of ketone has been purified by filtration through a pad of silica topped with celite and eluting with Heptane:EtOAc 1:1. LCMS: ACE 3 C8, 50×3.0 mm, 10% to 97% acetonitrile in 0.1% TFA in water, 1 mL/min; Rt=2.091.

Example 3

Synthesis of Picropodophyllin, i.e. (11S,15R)-16-hydroxy-10-(3,4,5-trimethoxyphenyl)-4,6,13-trioxatetracyclo[7.7.0.0^{3,7}.0^{11,15}]hexadeca-1,3(7),8-trien-12-one

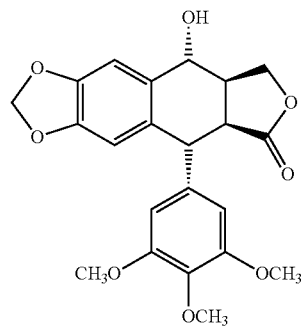

(11R,15S)-16-(3,4,5-trimethoxyphenyl)-4,6,13-trioxatetracyclo[7.7.0.0^{3,7}.0^{11,15}]hexadeca-1,3(7),8-triene-10,14-dione obtained in Example 2 (848 mg, 2.06 mmol) was suspended in methanol (50 mL) and cooled to 0° C. Sodium borohydride (117 mg, 3.08 mmol) was added and the suspension stirred over night. The reaction mixture was stirred at 0° C. for 3 h and was quenched by addition of 0.1 M hydrochloric acid. The product precipitated as white solid. The crude product was washed with methanol-water and purified by silica chromatography Pentane:EtOAc 1:3→1:5 to 221 mg of the title product (26%). LCMS analysis using ACE 3 C8, 50×3.0 mm, 10%-97% acetonitrile in 0.1% TFA in water, 1 mL/min showed 97% chromatographic purity; MS [M-OH$^-$]$^+$397 and [M+1]$^+$415. $^1$H-NMR (400 MHz, DMSO-d$^6$): d [ppm]=2.50-2.58 (m, 1H, overlapping with solvent residue signal), 3.42 (dd, 1H), 3.70 (s, 3H), 3.76 (s, 6H), 3.92 (d, 1H), 3.98 (bs, 1H), 4.36 (d, 1H), 4.41 (dd, 1H), 4.51 (dd, 1H), 5.42 (app. d, 2H), 6.03 (s, 1H), 6.50 (s, 2H), 7.08 (s, 1H).

Example 4

Synthesis of (11S,15S)-16-methylidene-10-(3,4,5-trimethoxyphenyl)-4,6,13-trioxatetracyclo[7.7.0.0^{3,7}.0^{11,15}]hexadeca-1,3(7),8-trien-12-one

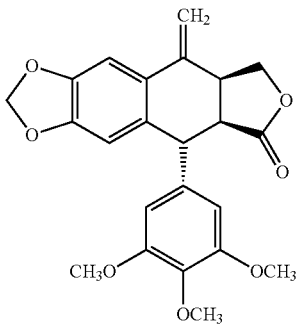

6-{[(4R)-4-ethenyl-2-oxooxolane-3-yl](3,4,5-trimethoxyphenyl)methyl}-2H-1,3-benzodioxol-5-yl trifluoromethanesulfonate (obtained according to Stadler, D.; Bach, T. *Angew. Chem., Int. Ed.,* 2008, 47, 7557-7559.) (6.70 g, 11.95 mmol) was dissolved in 95% ethanol (250 mL). Anhydrous sodium carbonate (3.80 g, 35.85 mmol) and Herrmann-Beller catalyst (CAS#172418-32-5) (0.45 g, 0.60 mmol) were added and the resulting mixture heated at reflux for 15 h. Upon cooling, the mixture was filtered through a pad of Celite and eluted with ethanol (100 mL). The filtrate was concentrated to give a solid (3.08 g). Yield: 63% The obtained material was used as such in the next step. An analytical sample was obtained by silica chromatography eluting with pentane:ethylacetate 1:1→1:2.

LCMS: ACE 3 C8, 50×3.0 mm, 10%-97% methanol in 0.1% TFA in water, 1 mL/min; 80%, MS: 428 (100), 411, 429

$^1$H-NMR (400 MHz, CDCl$_3$): δ [ppm]=3.67-3.82 (m, 3H), 3.85 (s, 6H), 3.90 (s, 3H), 3.98 (app. s, 1H), 4.0 (d, 1H), 4.95 (d, 1H), 5.11 (d, 1H), 5.92 (app. s, 1H), 5.94 (app. s, 1H), 6.23 (s, 1H), 6.50-6.55 (m, 2H), 6.85 (s, 1H)

Example 5

Synthesis of (11R,15S)-16-(3,4,5-trimethoxyphenyl)-4,6,13-trioxatetracyclo[7.7.0.0^{3,7}.0^{11,15}]hexadeca-1,3(7),8-triene-10,14-dione

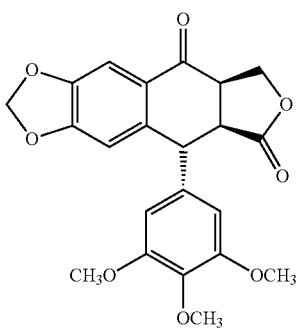

(11S,15S)-16-methylidene-10-(3,4,5-trimethoxyphenyl)-4,6,13-trioxatetracyclo[7.7.0.0^{3,7}.0^{11,15}]hexadeca-1,3(7),8-trien-12-one obtained in Example 4 (6.00 g, 14.63 mmol) and N-methyl-morpholine-oxide (50 wt-% solution in water, 9.01 mL, 43.90 mmol) were suspended in dichloromethane (100 mL). Osmium tetroxide (4 wt-% solution in water, 4.54 mL, 0.73 mmol) was added. The mixture was stirred at r.t. for 4 h. Sodium perioidate (6.26 g, 29.26 mmol) was added and the mixture stirred at r.t. for 1 h. The reaction was quenched by aqueous sodium thiosulfate (100 mL) and the phases separated. The water-phase was extracted with dichloromethane (3×100 mL) and the combined organic phases washed with brine, dried with magnesium sulfate, filtered and evaporated. The material was purified by filtration over a pad of silica gel, which was eluted with 50% ethylacetate in hexane. The filtrate was concentrated to give a solid (5.43 g). Yield: 90%

The obtained material was used as such in the next step.

LCMS: ACE 3 C8, 50×3.0 mm, 10%-97% methanol in 0.1% TFA in water, 1 mL/min; 80%, MS: 413 (100)

Example 6

Synthesis of Picropodophyllin, i.e. (11S,15R)-16-hydroxy-10-(3,4,5-trimethoxyphenyl)-4,6,13-trioxatetracyclo[7.7.0.0^{3,7}.0^{11,15}]hexadeca-1,3(7),8-trien-12-one

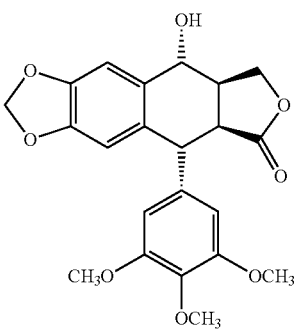

(11R,15S)-16-(3,4,5-trimethoxyphenyl)-4,6,13-trioxatetracyclo-[7.7.0.0^{3,7}.0^{11,15}]hexadeca-1,3(7),8-triene-10,14-dione obtained in analogy with Example 5 (40 g, 97.09 mmol) was suspended in methanol (700 mL) and the resulting mixture cooled to 0° C. Sodium borohydride (7.39 g, 194.18 mmol) was added in portions over 2 h and the resulting mixture stirred at r.t. overnight. Aqueous ammonium acetate (1 M, 200 mL) was added and the formed precipitate collected by filtration. The filter-cake was washed with 50 vol-% methanol in water (4×50 mL) and dried to constant weight under vacuum overnight to give a solid. The mother liquid was extracted with dichloromethane (3×500 mL); the organic solution was washed with brine and dried over anhydrous sodium sulfate. After filtration and concentration, the residue was combined with the dried solid and recrystallized from dichloromethane and hexane to afford a white solid (32.3 g). Yield: 80.4%

LCMS ACE 3 C8, 50×3.0 mm, 10%-97% acetonitrile in 0.1% TFA in water, 1 mL/min showed 97% chromatographic purity, MS [M+NH$_4$]$^+$432 (100), [M-OH]$^+$397

$^1$H-NMR (400 MHz, DMSO-d$_6$): δ [ppm]=2.50-2.58 (m, 1H, overlapping with solvent residue signal), 3.42 (dd, 1H), 3.70 (s, 3H), 3.76 (s, 6H), 3.92 (d, 1H), 3.98 (bs, 1H), 4.36 (d, 1H), 4.41 (dd, 1H), 4.51 (dd, 1H), 5.42 (app. d, 2H), 6.03 (s, 1H), 6.50 (s, 2H), 7.08 (s, 1H)

Specific rotation: [α]$^{28}_D$ (c=0.27 in chloroform)+13.0°

The invention claimed is:

1. A one-pot process for the preparation of a compound of Formula (I)

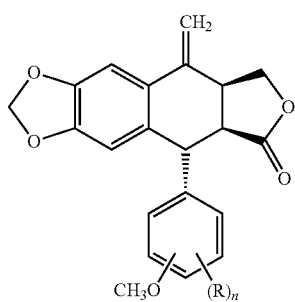

wherein:

R, which may be the same or different, is selected from the group consisting of OH, OCH$_3$, OCH$_2$CH$_3$, F, Cl, CH$_3$ and CF$_3$, and n is 0, 1, 2, 3, or 4;

the process comprising cyclization of a compound of Formula (II)

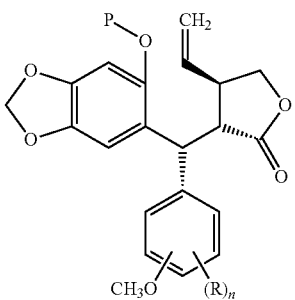

wherein:

R and n are as defined for Formula (I); and

P is an activating group;

in the presence of i. a base;

ii. a protic solvent, or a mixture of a protic and an aprotic solvent; and iii. a transition metal component;

wherein the process is performed under Heck reaction conditions.

2. The process according to claim 1, wherein the process comprises cyclizing a compound of Formula (IV)

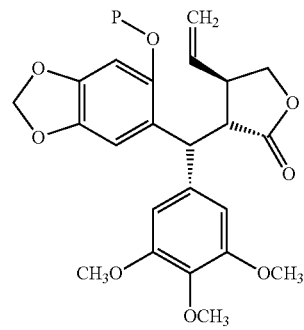

to yield a compound of Formula (III)

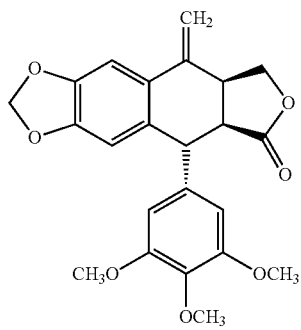

3. The process according to claim 1, wherein the transition metal component is selected from the group consisting of Pd(0), a compound containing Pd(II), a compound containing Pd(0), a mixture of compounds containing Pd(II) and Pd(0), and a mixture of Pd(0) and a compound containing Pd(II) and/or Pd(0).

4. The process according to claim 1, wherein the transition metal component is Ni(0) or Ni(II).

5. The process according to claim 3, wherein the transition metal component is the Herrmann-Beller catalyst.

6. The process according to claim 3, wherein the transition metal component is Pd-118.

7. The process according to claim 1, wherein the activating group P is selected from the group consisting of trifluoromethanesulfonate, methanesulfonate, ethanesulfonate, benzenesulfonate, toluenesulfonate and 4-nitrobenzenesulfonate.

8. The process according to claim 1, wherein the base is an inorganic base.

9. The process according to claim 8, wherein the base is selected from the group consisting of K$_2$CO$_3$, Na$_2$CO$_3$, KHCO$_3$, NaHCO$_3$, NaOH, Cs$_2$CO$_3$, KOH, NaOH, Na$_3$PO$_4$, Na$_2$HPO$_4$, K$_3$PO$_4$, K$_2$HPO$_4$, and NH$_4$OH.

10. The process according to claim 1, wherein the base is an amine base.

11. The process according to claim 10, wherein the amine base is selected from the group consisting of ammonia, trimethyl amine, triethyl amine, and diisopropyl ethylamine.

12. The process according to claim 1, wherein the transition metal component is selected from the group consisting of Pd(dppf).DCM, tetrakis(triphenylphosphine)Pd(0), Pd$_2$(dba)$_3$, dichlorobis(triphenylphosphine)-palladium (0), palladium(II) acetate, palladium(II) acetate triphenylphosphine, palladium(II) chloride, palladium(II) chloride triphenylphosphine, and palladium black.

13. The process according to claim 1, wherein the protic solvent is selected from the group consisting of methanol, ethanol, propanol, isopropanol, butanol and tert-butanol.

14. The process according to claim 1, wherein the solvent comprises 0.001-50 vol-% of water.

15. The process according to claim 14, wherein the solvent comprises 2-20 vol-% of water.

16. The process according to claim 14, wherein the solvent comprises 0.001-20 vol-% of water.

17. The process according to claim 15, wherein the solvent comprises 5 vol-% of water.

18. The process according to claim 1, further comprising the step of heating the reaction mixture during the cyclization of the compound of Formula (II).

19. The process according to claim 18, wherein said cyclization takes place at a temperature of from room temperature to 150 °C.

20. The process according to claim 19, wherein said cyclization takes place at a temperature of from 40° C. to 120° C.

21. The process according to claim 19, wherein said cyclization takes place at a temperature of from 30° C. to 100° C.

22. The process according to claim 21, wherein said cyclization takes place at a temperature of from 40° C. to 90° C.

23. The process according to claim 22, wherein said cyclization takes place at a temperature of from 50° C. to 80° C.

24. The process according to claim 23, wherein said cyclization takes place at a temperature of from 60° C. to 80° C.

25. The process according to claim 24, wherein said cyclization takes place at a temperature of from 70° C. to 80° C.

26. A method of making picropodophyllin, the method comprising utilizing a process according to claim 1.

* * * * *